United States Patent [19]

Cannell et al.

[11] 4,424,820

[45] * Jan. 10, 1984

[54] HAIR STRAIGHTENING COMPOSITIONS CONTAINING FATTY ACID LACTYLATES AND GLYCOLATES AND THEIR METHOD OF USE

[75] Inventors: David W. Cannell, Los Angeles; Geoffrey R. Hawkins, Granada Hills, both of Calif.

[73] Assignee: Redken Laboratories, Inc., Canoga Park, Calif.

[*] Notice: The portion of the term of this patent subsequent to Nov. 24, 1998 has been disclaimed.

[21] Appl. No.: 230,754

[22] Filed: Feb. 2, 1981

Related U.S. Application Data

[63] Continuation-in-part of Ser. No. 118,231, Feb. 4, 1980, Pat. No. 4,301,820.

[51] Int. Cl.$^3$ .......................... A45D 7/04; A61K 7/09
[52] U.S. Cl. ............................................. 132/7; 424/72
[58] Field of Search ................................ 424/72; 132/7

[56] References Cited

U.S. PATENT DOCUMENTS

| | | | |
|---|---|---|---|
| 3,728,447 | 4/1973 | Osipow et al. | 424/70 |
| 4,237,910 | 12/1980 | Khalil et al. | 424/70 |
| 4,301,820 | 11/1981 | Cannell et al. | 132/7 |

FOREIGN PATENT DOCUMENTS 1008731 11/1965 United Kingdom ................. 424/72

*Primary Examiner*—Dale R. Ore
*Attorney, Agent, or Firm*—Christie, Parker & Hale

[57] ABSTRACT

Fatty acid lactylates and/or glycolates are combined with sodium hydroxide or at least one reducing agent for hair and used in a hair straightening operation.

49 Claims, No Drawings

HAIR STRAIGHTENING COMPOSITIONS CONTAINING FATTY ACID LACTYLATES AND GLYCOLATES AND THEIR METHOD OF USE

CROSS-REFERENCE TO RELATED APPLICATIONS

This is a continuation-in-part of Application Ser. No. 118,231, filed Feb. 4, 1980, now U.S. Pat. No. 4,301,920, incorporated herein by reference.

BACKGROUND OF THE INVENTION

Permanent waving is a process whereby a reducing agent is applied to mandrel-wound hair to open the disulfide linkages of the hair structure which are formed by the amino acid cystine. The protein chains flow under tension to assume the imparted shape. After rinsing, an oxidizing agent is then applied to re-establish or close the disulfide linkages which, in effect, hardens the protein structure to lock it into the new position.

Hair can be relaxed or straightened by a converse process whereby the hair is chemically acted upon when the hair is straight or at a curl having a radius of curvature greater than that existing in the hair. To this end, the hair can be held straight or wound on rods or mandrels of large diameter.

An essential element of a hair straightening composition is sodium hydroxide or a reducing agent. Among the reducing agents there may be mentioned thioglycolic acid, salts, and esters thereof; thiolactic acid and salts thereof; sulfide salts; bisulfite salts, cysteine, and the like. Aside from sodium hydroxide, the bulk of the compositions for straightening hair are based on thioglycolic acid, salts, or esters thereof, or the bisulfite salts.

The compositions used for relaxing or straightening hair are normally provided as a gel or a cream which serves to mechanically hold the hair in a straightened state during chemical attack. Sodium hydroxide relaxers are generally cream compositions at concentrations up to 3%, preferably about 2 to about 3%, NaOH. Sodium hydroxide attacks the disulfide bond to produce lanthionine which now crosslinks the hair in its straightened form. The generalized reaction is:

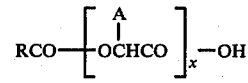

cystine          lanthionine

Following straightening, an acid rinse is usually applied to neutralize excess alkali.

The hair may be straightened with thioglycolates under acid conditions. To this end, citric, lactic, phosphoric, and weak carboxylic acids are used as common acidifying agents. Bisulfite straighteners are also acid, namely at a pH from about 5.5 to 6.9, and are applied at room temperature.

As with sodium hydroxide compositions, contact with the reducing agent may range from 10 minutes or less to 50 minutes or more. After an appropriate time of contact, the reducing agent is rinsed from the hair, and an oxidizing agent is applied to close the disulfide bonds and set the straightened hair. Excess oxidizing agent is then rinsed from the hair, and the hair is dried. The most common oxidizing agents are hydrogen peroxide and bromate salts. Peroxides are applied over a pH range from 2.5 to about 4.0 and bromates from a pH of about 5.0 to about 8.0. Application is at ambient or elevated temperatures.

In general, sodium hydroxide is the most effective straightener but is also the most damaging to hair and most likely to irritate the skin. Thioglycolate and alkali bisulfite straighteners do not produce the same degree of straightening but relax the curl from a tighter to a looser wave pattern.

All forms of hair straightening suffer by reversion. As the straightened or relaxed hair is subjected to shampooing, heat or high humidity, it reverts to some degree back to its curly form.

SUMMARY OF THE INVENTION

It has now been surprisingly found that the lactylates and glycolates, when incorporated as part of a hair straightening agent, composition or solution applied to hair, will impart unexpected and desirable qualities to the hair when processed through a straightening operation. The most significant effects are the degree of straightening and retention of the straightened state, in that there is an exceptional resistance to reversion under conditions of both high and low humidity.

The compositions provided in accordance with the instant invention comprise an aqueous solution of sodium hydroxide or at least one hair reducing agent in combination with at least one fatty acid lactylate and/or glycolate of the formula:

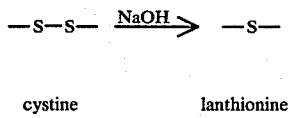

wherein RCO is an acyl radical of a fatty acid having from about 6 to about 22 carbon atoms, A is CH$_3$ or H, and x has a value of from 1 to about 4, as well as the ammonium, alkali metal, and amine salts thereof, the total of lactylates and/or glycolates added being sufficient to increase the degree of straightening of the hair as compared to the degree of straightening using the same composition in the absence of a fatty acid lactylate and/or glycolate. The amine salts, when used, are the physiologically acceptable amine salts. The compositions based on a reducing agent preferably contain an emulsifier to improve compatibility of the components of the hair straightening composition. Further, the compositions are preferably used at a viscosity sufficient to hold hair in a straightened state and, to this end, are usually applied as a cream or a gel.

Besides sodium hydroxide, the reducing agents used are preferably thioglycolic acid, a salt or ester thereof, or an alkali bisulfite, preferably sodium bisulfite. For compositions containing a reducing agent, glycerol monothioglycolate or ammonium monothioglycolate are presently preferred for acid compositions. Ammonium monothioglycolate and monoethanolamine thioglycolate may be used in alkaline compositions.

The presently preferred fatty acid lactylate is sodium isostearoyl-2-lactylate.

The hair straightening process of the invention includes the steps of reacting hair in a straightened state with a solution of sodium hydroxide or a reducing agent for hair, which solution includes at least one fatty acid, lactylate and/or glycolate, for a time sufficient to cause, in the instante of sodium hydroxide, the formation of lanthionine links or, with a reducer, to open the disulfide linkages of the hair, and later followed by the step of subsequently closing the disulfide linkages of the hair by application of an oxidizing agent to the hair to set the hair in the desired straightened state. The fatty acid lactylates and/or glycolates used in the practice of the invention serve to materially increase the degree of swelling of the hair. This permits faster penetration by the sodium hydroxide, or reducing agent, resulting in more efficient straightening.

When a reducing composition based on glycerol monothioglycolate is employed, the reducing agent and fatty acid lactylate and/or glycolate serve as a first component which is combined with a balancer compound of the balance of the constituents forming a net reducing composition for application to the surface of hair in a conventional manner.

After the hair is straightened and rinsed, the hair is oxidized using hydrogen peroxide or a bromate salt to set the hair. Rinsing is employed following oxidation, and the hair is dried.

Where sodium hydroxide is used, the hair is neutralized using an acid solution, then dried.

DETAILED DESCRIPTION

The present invention is directed to the straightening of hair, and is based on the use of fatty acid lactylates and glycolates of the formula:

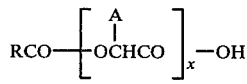

wherein RCO is the acyl radical of a fatty acid containing from about 6 to about 22 carbon atoms, A is $CH_3$ or H, and x is a number from 1 to about 4, as well as their ammonium, alkali metal, and physiologically acceptable amine salts, as humectants, introduced by acid or alkaline hair straightening solutions to impart a high degree of straightening to hair which remains at a high level, despite gross fluctuations in humidity.

The compounds useful in accordance with the present invention are described in greater detail in U.S. Pat. No. 3,728,447 to Osipow et al, incorporated herein by reference, and are produced by methods described in U.S. Pat. No. 3,733,252, also incorporated hereby by reference.

Suitable fatty acid lactylates and glycolates which may be mentioned include isostearoyl-2-lactylate, caproyl-2-lactylate, caprylyl-2-lactylate, capryl-2-lactylate, lauryl-1-lactylate, lauryl-2-lactylate, lauryl-3-lactylate, lauryl-4-lactylate, myristyl-1-lactylate, myristyl-2-lactylate, oleoyl-2-lactylate, palmityl-2-lactylate, stearyl-2-lactylate, behenyl-2-lactylate, lauryl-1-glycolate, lauryl/myristyl-1-glycolate, capryl-1-glycolate; salts thereof, and the like. Sodium isostearoyl-2-lactylate is presently preferred.

The amount of lactylate and/or glycolate to be incorporated into the hair straightening composition is an amount sufficient to impart increased straightening as compared to the same hair straightening composition used without the lactylate and/or glycolate.

The hair straightening compositions are based on sodium hydroxide or a reducing agent for hair, the latter used in conjunction with an oxidizing agent.

Sodium hydroxide reacts with the hair to form lanthionine links, and is applied from solution. Concentration is typically up to about 3% by weight sodium hydroxide, preferably from about 2 to about 3% by weight of solution.

The reducing agents, by contrast, open the disulfide linkages of the hair. The protein chains of the hair assume the imparted straightened shape, and the linkages are then closed to cause hair to retain a straightened shape. The preferred reducing agents are thioglycolic acid, salts of thioglycolic acid, esters of thioglycolic acid, bisulfite salts such as sodium bisulfite, ammonium bisulfite and the like. Ammonium monothioglycolate or glycerol monothioglycolate are presently preferred. Preferably, the ratio of moles of reducing agent to lactylate and/or glycolate in the composition is from about 15 to about 80.

Generally, the total concentration of lactylates and/or glycolates in the hair straightening composition employed range from about 0.1 to about 2% by weight of solution, preferably from 0.5 to about 1.5% by weight.

The compositions are normally formulated to a viscosity sufficient to form a gel or a cream which retains hair in a straightened state during chemical action and until removed by rinsing or application of the oxidizing agent. Sodium hydroxide compositions are removed by acid shampoos or rinses, which neutralize the excess alkali present in the hair.

Because the compositions containing a reducing agent have been observed to separate on standing, it is desired to incorporate a minor amount of an emulsifier to stabilize the solution against separation. Emulsifiers, such as oleth-20, may be used, and have been established not to have an adverse effect upon straightening efficiency.

When straightening solutions based on glycerol monothioglycolate are used, the fatty acid lactylates and/or glycolates used are combined with the reducing agent, which forms one component of a two-component system. The second component used in forming the net reducing composition is termed the balancer, and it is presently preferred that the balancer be an aqueous ammoniacal solution, preferably buffered. The component comprising the humectant compound reducing agent and, if present, the emulsifier, is added to the balancer to provide a net solution at a suitable pH for application to the hair.

For other reducing agents, e.g., ammonium monothioglycolate and sodium hydroxide, a one-compound system may be employed.

For acid straightening solutions, the pH may range from 5.0 to 6.9, preferably from 6.5 to 6.9, and more preferably, 6.7 to 6.9. From sodium hydroxide and other alkaline straighteners, pH may range from 7.5 to 12.0 or more. In this instance, it is not necessary to employ a balancing solution, and a one-component system is employed.

The straightening process involves holding the hair straight or to a radius of curvature greater than the radius of curvature of natural or induced curls of the hair. To this end, oversized rollers or mandrels can be used in the straightening process.

Straightening can be carried out at ambient to elevated temperatures. The hair is placed in the straightened state by the composition itself and/or by other mechanical means, and is allowed to remain in contact with the acting solution for periods of up to 50 minutes or more. Then the composition is removed. In the instance of a sodium hydroxide solution, this is preferably accomplished using an acid rinse or shampoo to remove excess alkali. When a reducing agent for hair is employed, the open disulfide linkages are closed by application of an oxidizing agent which is then rinsed from the hair.

As established by the following Examples and Controls, the use of fatty acid lactylates and/or glycolates impart, as compared to hair straightening compositions used without them, a higher degree of initial straightening and greater retention of straightness under humid and dry conditions. They cause hair to take up and retain moisture without adverse loss of straightness.

Without being bound by theory, results suggest that the fatty acid lactylates and/or glycolates either bind water, rather than allow water to relax the hydrogen bonds of the protein structure, or shield the hydrogen bonds from water.

EXAMPLES AND CONTROLS

There were formulated cream hair straightening compositions of the following formulations given below. Composition A, containing sodium isostearoyl-2-lactylate (ISL), was used for the Examples which illustrate the invention, while an essentially identical composition (Composition B), without ISL, was used for the Controls.

| Cream Ingredient | Composition A % by Wgt | Composition B % by Wgt |
| --- | --- | --- |
| Water | 42.25 | 43.35 |
| Sodium Hydroxide | 2.20 | 2.20 |
| Sodium Lauryl Ether Sulfate | 6.00 | 6.00 |
| Hydrolyzed Animal Protein | 1.00 | 1.00 |
| Mineral Oil | 21.30 | 21.30 |
| Petrolatum | 8.00 | 8.00 |
| Squalane | 3.00 | 3.00 |
| Lauryl Alcohol | 1.25 | 1.25 |
| Lanolin Fatty Acids | 2.00 | 2.00 |
| Cetyl Alcohol | 12.00 | 12.00 |
| Sodium Isostearoyl-2-lactylate | 1.00 | — |

EXAMPLE 1 AND CONTROL A

Each of Compositions A and B were applied to tresses of Negroid kinky hair which had an initial length of 12.0 cm when dry. These creams were worked through the tresses with a comb for 25 minutes to obtain a straight configuration. The length of extended hair was 22.5 cm for Example 1 and 21.5 cm for Control A.

The tresses were then washed with an acidic shampoo to remove the cream and excess alkali. After washing, the tress of Example 1 was 22.0 cm, while that of Control A was 19.5 cm. The degree of straightening was determined by the formula:

$$\text{Degree of Straightening} = \frac{\text{length}_{(final)} - \text{length}_{(initial)}}{\text{length}_{(initial)}}$$

The results are reported below:

| | Degree of Straightening |
| --- | --- |
| Example 1 (Comp. A) | 83.3% extension |
| Control A (Comp. B) | 62.5% extension |

This demonstrates a more efficient straightening for the composition containing ISL at ambient humidity.

EXAMPLE 2 AND CONTROL B

The tresses were then subjected to 90% RH[1] for five hours and remeasured, and the degree of straightening was recalculated.

[1]RH=Relative Humidity

The lengths were now 17.0 cm for Control B and 20.5 cm for Example 2.

| | Degree of Straightening |
| --- | --- |
| Example 2 (Comp. A) | 70.8% extension |
| Control B (Comp. B) | 41.6% extension |

This demonstrates the resistance to reversion at high humidity.

EXAMPLE 3 AND CONTROL C

The tresses were then desiccated for 7 hours and 0–5% RH. The length of Example 3 was 18.0 cm, and Control C was 16.5 cm. Degree of straightening is reported below:

| | Degree of Straightening |
| --- | --- |
| Example 3 (Comp. A) | 50.0% extension |
| Control C (Comp. B) | 37.5% extension |

This demonstrates greater resistance to reversion for the ISL compositions at low humidity.

EXAMPLE 4 AND CONTROL D

A second pair of tresses were treated as described for Example 1 and Control A. The initial weight of the tress treated with Composition A was 0.638 gm. The initial weight of the tress treated with Composition B was 0.672 gm. After treatment, the tresses were blotted and placed at 0–5% RH for 4 hours. They were then reweighed. The results are shown below:

| | Initial Weight | Final Weight | % Loss of Moisture |
| --- | --- | --- | --- |
| Example 4* | 0.638 gm | 0.572 gm | 10.3 |
| Control D** | 0.672 gm | 0.510 gm | 24.1 |

The hair treated with Composition A retained more moisture and remained straighter than hair treated with Composition B.

EXAMPLE 5 AND CONTROL E

The same tresses were then exposed to 90% RH for 4 hours. The results are shown below:

| | Initial Weight | Final Weight | % Moisture Gain |
| --- | --- | --- | --- |
| Example 5* | 0.638 gm | 0.698 gm | 9.3 |
| Control E** | 0.672 | 0.693 gm | 3.1 |

*Comp. A
**Comp. B

The hair treated with Composition A gained more moisture, yet remained straighter.

What is claimed is:

1. In an aqueous composition for the straightening of hair which contains a hair reactant for straightening hair, selected from the group consisting of at least one reducing agent for hair and sodium hydroxide, wherein the improvement comprises having in the composition for straightening hair at least one humectant compound selected from the group consisting of fatty acid lactylates and fatty acid glycolates of the formula:

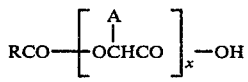

wherein RCO is an acyl radical of a fatty acid having from about 6 to about 22 carbon atoms, A is $CH_3$ or H, and x has a value of from about 1 to about 4, and ammonium, alkali metal and amine salts thereof; the total amount of humectant compound included in said composition being sufficient to impart to hair, straightened using the composition, a higher degree of straightening as compared to hair straightened using the composition for straightening hair in the absence of said humectant compound.

2. A composition as claimed in claim 1 in which the reducing agent for hair is selected from the group consisting of thioglycolic acid, a salt of thioglycolic acid, an ester of thioglycolic acid and bisulfite salts.

3. A composition as claimed in claim 1 in which the humectant compound is sodium isostearoyl-2-lactylate.

4. A composition as claimed in claim 2 in which the humectant compound is sodium isostearoyl-2-lactylate.

5. A composition as claimed in claim 2 in which the reducing agent is glycerolmonothioglycolate.

6. A composition as claimed in claim 2 in which an emulsifying agent is present.

7. A composition as claimed in claim 6 in which the emulsifying agent is oleth-20.

8. A composition as claimed in claim 5 in which an emulsifying agent is present.

9. A composition as claimed in claim 8 in which the emulsifying agent is oleth-20.

10. In a composition for the straightening of hair which is an aqueous solution containing sodium hydroxide present in a concentration sufficient to straighten hair, wherein the improvement comprises having in the composition for straightening hair at least one humectant compound selected from the group consisting of fatty acid lactylates and fatty acid glycolates of the formula:

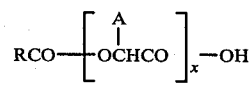

wherein RCO is an acyl radical of a fatty acid having from about 6 to about 22 carbon atoms, A is $CH_3$ or H, and x has a value of from 1 to about 4, and ammonium, alkali metal and amine salts thereof present in a quantity sufficient to impart to hair, straightened using the composition, a higher degree of straghtening as compared to hair straightened using the composition for straightening hair in the absence of said humectant compound, said solution having a viscosity sufficient to maintain curled hair in a substantially straightened state on application of the solution thereto for reaction of sodium hydroxide with the hair to straighten the hair.

11. A composition as claimed in claim 10 in which sodium hydroxide is present in a concentration up to about 3% by weight of the solution.

12. A composition as claimed in claim 10 in which sodium hydroxide is present in a concentration of from about 2 to about 3% by weight of the solution.

13. A composition as claimed in claim 10 in which the humectant compound is sodium isostearoyl-2-lactylate.

14. A composition as claimed in claim 11 in which the humectant compound is sodium isostearoyl-2-lactylate.

15. In an aqueous hair straightening system which consists of a hair straightening composition containing at least one reducing agent for hair, selected from the group consisting of thioglycolic acid, salts of thioglycolic acid, esters of thioglycolic acid and bisulfite salts, wherein the improvement comprises providing in the hair straightening composition at least one humectant compound selected from the group consisting of fatty acid lactylates and fatty acid glycolates of the formula:

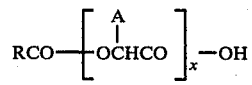

wherein RCO is an acyl radical of a fatty acid having from about 6 to about 22 carbon atoms, A is $CH_3$ or H, and x has a value of from 1 to about 4, and ammonium, alkali metal and amine salts thereof; the total amount of humectant compound included in said composition being sufficient to impart to hair, straightened using the net composition, a higher degree of straightening as compared to hair straightened using the hair straightening composition in the absence of said humectant compound, the hair straightening composition having a viscosity, when applied to hair, sufficient to maintain curled hair in a substantially straightened state during reaction of the contained reducing agent with the hair.

16. A hair straightening system as claimed in claim 15 in which the humectant compound is sodium isostearoyl-2-lactylate.

17. A hair straightening system as claimed in claim 16 in which the reducing agent is selected from the group consisting of glycerol monothioglycolate and ammonium monothioglycolate.

18. A hair straightening system as claimed in claim 15 in which the composition includes an emulsifying agent.

19. A hair straightening system as claimed in claim 18 in which the emulsifying agent is oleth-20.

20. A hair straightening system as claimed in claim 17 in which the composition includes an emulsifying agent.

21. A hair straightening system as claimed in claim 20 in which the emulsifying agent is oleth-20.

22. A hair straightening system as claimed in claim 17 in which the reducing agent is glycerol monothioglycolate further includes a balancer for addition to the combination of the glycerol monothioglycolate and sodium isostearoyl-2-lactylate.

23. A hair straightening system as claimed in claim 22 in which the balancer is a buffered aqueous ammoniacal solution.

24. In an aqueous hair straightening system which consists of a hair straightening composition containing at least one reducing agent for hair, selected from the group consisting of thioglycolic acid, salts of thioglycolic acid, esters of thioglycolic acid and bisulfite salts, wherein the improvement comprises providing in the hair straightening composition at least one humectant compound selected from the group consisting of fatty acid lactylates and fatty acid glycolates of the formula:

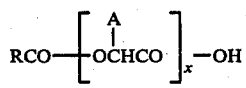

wherein RCO is acyl radical of a fatty acid having from about 6 to about 22 carbon atoms, A is $CH_3$ or H, and x has a value of from 1 to about 4, and ammonium, alkali metal and amine salts thereof; the ratio of total moles of reducing agent to total moles of humectant compound in said hair straightening composition having a viscosity, when applied to hair, sufficient to maintain curled hair in a substantially straightened state during reaction of the contained reducing agent with the hair.

25. A hair straightening system as claimed in claim 24 in which the humectant compound is sodium isostearoyl-2-lactylate.

26. A hair straightening system as claimed in claim 25 in which the reducing agent is selected from the group consisting of glycerol monothioglycolate and ammonium monothioglycolate.

27. A hair straightening system as claimed in claim 24 in which the composition includes an emulsifying agent.

28. A hair straightening system as claimed in claim 27 in which the emulsifying agent is oleth-20.

29. A hair straightening system as claimed in claim 26 in which the composition includes an emulsifying agent.

30. A hair straightening system as claimed in claim 29 in which the emulsifying agent is oleth-20.

31. A hair straightening system as claimed in claim 26 in which the reducing agent is glycerol monothioglycolate further includes a balancer for addition to the combination of the glycerol monothioglycolate and sodium isostearoyl-2-lactylate.

32. A hair straightening system as claimed in claim 31 in which the balancer is a buffered aqueous ammoniacal solution.

33. In a process for the straightening of hair which includes the step of contacting straightened hair with an aqueous hair straightening solution containing a reducing agent for hair, selected from the group consisting of thioglycolic acid, salts of thioglycolic acid, esters of thioglycolic acid and bisulfite salts, the improvement of which comprises providing in the aqueous hair straightening solution at least one humectant compound selected from the group consisting of fatty acid lactylates and fatty acid glycolates of the formula:

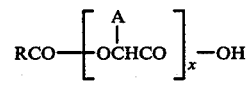

wherein RCO is acyl radical of a fatty acid having from about 6 to about 22 carbon atoms, A is $CH_3$ or H, and x has a value of from 1 to about 4, and ammonium, alkali metal and amine salts thereof, to open the disulfide linkages of the straightened hair by application of an oxidizing agent of the hair to set the hair in a straightened state; the total amount of humectant compound included in said hair straightening solution of a reducing agent for hair being sufficient to increase the degree of straightening of the hair as compared to the degree of straightening achieved with the hair straightening solution in the absence of the humectant compound.

34. A process as claimed in claim 33 in which the humectant compound is sodium isostearoyl-2-lactylate.

35. A process as claimed in claim 33 in which said solution of a reducing agent for hair contains an emulsifying agent.

36. A process as claimed in claim 35 in which the emulsifying agent is oleth-20.

37. A process as claimed in claim 34 in which said solution of a reducing agent for hair contains an emulsifying agent.

38. A process as claimed in claim 37 in which the emulsifying agent is oleth-20.

39. In a process for the straightening of hair which comprises the steps of forming straightened hair by application of an aqueous hair straightening solution of a reducing agent for hair, selected from the group consisting of thioglycolic acid, salts of thioglycolic acid, esters of thioglycolic acid and bisulfite salts, followed by closing the disulfide linkages of the straightened hair by application of an oxidizing agent to the hair to set the hair in a straightened state, the improvement of which comprises providing in the aqueous hair straightening solution at least one humectant compound selected from the group consisting of fatty acid lactylates and fatty acid glycolates of the formula:

wherein RCO is an acyl radical of a fatty acid having from about 6 to about 22 carbon atoms, A is $CH_3$ or H, and x has a value of from 1 to about 4, and ammonium, alkali metal and amine salts thereof, in which the ratio of total moles of reducing agent to total moles of humectant compound in the solution of said reducing agent is about 15 to about 80, to open the disulfide linkages of the straightened hair.

40. A composition as claimed in claim 34 in which the humectant compound is sodium isostearoyl-2-lactylate.

41. A process as claimed in claim 39 in which said solution of a reducing agent for hair contains an emulsifying agent.

42. A process as claimed in claim 41 in which the emulsifying agent is oleth-20.

43. A process as claimed in claim 40 in which said solution of a reducing agent for hair contains an emulsifying agent.

44. A process as claimed in claim 43 in which the emulsifying agent is oleth-20.

45. In a process for the straightening of hair which includes the steps of forming straightened hair by application of an aqueous solution of sodium hydroxide present in a concentration sufficient to straighten hair, then removing the sodium hydroxide by application to the hair of an acid solution, the improvement of which comprises providing in the aqueous solution of sodium hydroxide at least one humectant compound selected from the group consisting of fatty acid lactylates and fatty acid glycolates of the formula:

wherein RCO is an acyl radical of a fatty acid having from about 6 to about 22 carbon atoms, A is $CH_3$ or H, and x has a value of from 1 to about 4, and ammonium, alkali metal and amine salts thereof.

46. A process as claimed in claim 45 in which sodium hydroxide is present in solution in a concentration up to about 3% by weight of the solution.

47. A process as claimed in claim 45 in which sodium hydroxide is present in solution in a concentration of from about 2 to about 3% by weight of the solution.

48. A process as claimed in claim 45 in which the humectant compound is sodium isostearoyl-2-lactylate.

49. A process as claimed in claim 46 in which the humectant compound is sodium isostearoyl-2-lactylate.

* * * * *

UNITED STATES PATENT AND TRADEMARK OFFICE
CERTIFICATE OF CORRECTION

PATENT NO. : 4,424,820

DATED : January 10, 1984

INVENTOR(S) : David W. Cannell, Geoffrey R. Hawkins

It is certified that error appears in the above-identified patent and that said Letters Patent are hereby corrected as shown below:

Column 1, line 9, change "Pat. No. 4,301,920," to
    -- Pat. No. 4,301,820 --;
Column 1, lines 47-50, wavy lines omitted in example.
Column 3, line 1, change "instante" to -- instance --.
Column 9, line 14, after "composition" insert -- being
    from about 15 to about 80 --.

Signed and Sealed this

Twenty-first Day of October, 1986

[SEAL]

Attest:

DONALD J. QUIGG

Attesting Officer      Commissioner of Patents and Trademarks